United States Patent [19]

Raikhel et al.

[11] Patent Number: 5,187,262
[45] Date of Patent: Feb. 16, 1993

[54] CDNA ENCODING A POLYPEPTIDE INCLUDING A HEVEIN SEQUENCE

[75] Inventors: Natasha V. Raikhel, Okemos, Mich.; Willem F. Broekaert, Dilbeek, Belgium; Nam-Hai Chua, Scarsdale; Anil Kush, New York, both of N.Y.

[73] Assignee: Board of Trustees, operating Michigan State University, East Lansing, Mich.

[21] Appl. No.: 587,071

[22] Filed: Sep. 24, 1990

[51] Int. Cl.$^5$ .............................................. C07K 15/10
[52] U.S. Cl. .................................... 530/370; 530/379; 435/69.1
[58] Field of Search ................... 530/370, 379; 514/8, 514/12; 435/69.1

[56] References Cited

U.S. PATENT DOCUMENTS 4,727,028  2/1988  Santerre et al. ................. 435/240.2
4,800,159  1/1989  Mullis et al. ...................... 435/172.3

OTHER PUBLICATIONS

Broehaert, W. 1988. "Chitinases and Chitin-bending Lectin in Plants: A Biochemical and Physiological Study of their Role in the Natural Protection of Plants Against Fungi," Dissertation de Agricultura, Katholiehe Universiteit Leuven, pp. 1–125.
de Fay, E. & Jacob, J. L. (1989) in Physiology of Rubber Tree Latex, eds. d'Auzac, J., Jacob, J. L. & Chrestin, H. (CRC, Boca Raton, Fla.), pp. 3–14.
d'Auzac, J. & Jacob, J. L. (1989) in Physiology of Rubber Tree Latex, eds. d'Auzac, J., Jacob, J. L., & Chrestin, H. (CRC, Boca Raton, Fla.), pp. 59–88.
Archer, B. L., et al., J. Rubber Res. Inst. Malaya 21, 560–569 (1969).
Walujono, K., et al., in Proc. Internat. Rubber Conf. 518–531 (1975).
Wright, C. S., et al. Biochemistry 23, 280–287 (1984).
Raikhel & Wilkins, Proc. Natl. Acad. Sci. USA 84, 6745–6749 (1988).
Lerner, D. R., et al., Plant Physiol. 91, 124–129 (1989).
Wilkins, T. A., et al., Plant Cell 1, 541–549 (1989).

Chapot, M. P., et al., FEBS Lett. 195, 231–234 (1986).
Broglie, K. E., et al., Proc. Natl. Acad. Sci. USA 83, 6820–6824 (1986).
Shinshi, H. et al., Proc. Natl. Acad. Sci. USA 84, 89–93 (1987).
Parsons, T. J., et al. Proc. Natl. Acad. Sci. USA 86, 7895–7899 (1989).
Stanford, A., et al., Mol. Gen. Genet. 215, 200–208 (1989).

(List continued on next page.)

Primary Examiner—Robert A. Wax
Assistant Examiner—Keith C. Furman
Attorney, Agent, or Firm—Ian C. McLeod

[57] ABSTRACT

A cDNA clone (HEV1) encoding hevein was isolated via polymerase chain reaction (PCR) using mixed oligonucleotides corresponding to two regions of hevein as primers and a *Hevea brasiliensis* latex cDNA library as a template. HEV1 is 1018 nucleotides long and includes an open reading frame of 204 amino acids. The deduced amino acid sequence contains a putative signal sequence of 17 amino acid residues followed by a 187 amino acid polypeptide. The amino-terminal region (43 amino acids) is identical to hevein and shows homology to several chitin-binding proteins and to the amino-termini of wound-induced genes in potato and poplar. The carboxyl-terminal portion of the polypeptide (144 amino acids) is 74–79% homologous to the carboxyl-terminal region of wound-inducible genes of potato. Wounding, as well as application of the plant hormones abscisic acid and ethylene, resulted in accumulation of hevein transcripts in leaves, stems and latex, but not in roots, as shown by using the cDNA as a probe. A fusion protein was produced in *E. coli* from the protein of the present invention and maltose binding protein produced by the *E. coli*.

2 Claims, 6 Drawing Sheets

```
HEV1   M*NI****FIVVL*LC**LTGVAIAEQCGRQAGGKLCPNNLCCSQWGWCGSTDEYCSPDHNCQSNCKDSG
       | :    ::| ||  || || | ||||| || :  ||||||||:|||||| |||||  |||:| ||
WIN2   MVKLSCGPILLALVLCISLTSVANAQQCGRQRGGALSGNNLCCSQFGWCGSTPEYCSPSQGCQSQCTGSG

HEV1   EGVG*GGSASNVLATYHLYNSQDHGWDLNAASAYCSTWDANKPYSWRSKYGWTAFCGPVGAHGQSSCGKC
       | |||| || ||||:|| |  ||||||  ||||||||||||:||||||||||||| :|   |||||
WIN2   PDPGQGGSAQNVRATYHIYNPQNVGWDLNAVSAYCSTWDANKPYAWRSKYGWTAFCGPVGPRGRDSCGKC

HEV2   LSVTNTGTGAKTTVRIVDQCSNGGLDLDVNVFRQLDTDGKGYERGHITVNYQFVDCGDSFN*PLFSVMKSSVIN
       | |||| |||  ||||||||||||||||||||:||| |:|||| |  ||: ||||| ||| | ||  ||:
WIN2   LRVTNTRTGAQTTVRIVDQCSNGGLDLDINVFQQIDTDGVGNQQGHLIVNYQFVNCGDNVNVPLLSVV*DK**E
```

OTHER PUBLICATIONS

Weinstein, L. I., et al., Plant Physiol., 68, 358–363 (1981).

Coupe, M., et al. in Physiology of Rubber Tree Latex, eds. d'Auzac, J., et al. (CRC Press, Inc., Fla.) pp. 295–319 (1989).

Kush, A., et al., Proc. Natl. Acad. Sci. USA, 87 1787–1790 (1990).

Siflow, C. D., et al., Biochem. 18, 2725–2731 (1979).

Gubler, U., et al, Gene 25, 263–269 (1983).

Viera, J., et al., Methods Enzymol. 153 3–11 (1987).

Feinberg, A. P., et al. Anal. Biochem. 137, 266–267 (1985).

Raikhel, N. V., et al., Planta 176, 406–414 (1988).

Sanger, F., et al., Proc. Natl. Acad. Sci. USA 74, 5463–5467 (1977).

Mizusawa, S., et al., Nucl. Acids Res. 14, 1319–1324 (1986).

Dale, R. M. K., et al., Methods Enzymol. 155, 204–214 (1987).

Kirk, M. M., et al., Cell, 41, 419–428 (1985).

Molano et al, Anal. Biochem. 83, 648–656 (1977).

Boutry, M., et al., EMBO Journal 4, 2159–2165 (1985).

Guam et al, Gene 67, 21–30 (1988).

Hooft van Huijsduijnen, R. A. M., et al., Plant Mol. Biol. 9, 411–420 (1987).

Shinshi, H., et al., Plant Mol. Biol. 14, 357–368 (1990).

Broekaert, W. F., et al., Science 245, 1100–1102 (1989).

Schlumbaum, A., et al., Nature 324, 365–367 (1986).

Broekaert, W. F., et al. Physiol. Mol. Plant Pathol. 33, 319–331 (1988).

Graham, J. S., et al., Planta 169, 399–405 (1986).

Pena-Cortes, H., et al., Proc. Natl. Acad. Sci. USA 86, 9851–9855 (1989).

Boller, T., et al., Nature 286, 259–260 (1980).

Yang, S. F., et al. Annu. Rev. Plant Physiol. 35, 155–189 (1984).

Henstrand, J. M., et al, Plant Physiol. 91, 157–162 (1990).

Hedrick, S. A., et al., Plant Physiol. 86, 182–186 (1988).

Ecker, J. R., et al., Proc. Natl. Acad. Sci. USA 84, 5202–5206 (1987).

```
                                            10
Glu Gln Cys Gly Arg Gln Ala Gly Gly Lys Leu Cys Pro Asn Asn
        N-terminal
             20                                          30
Leu Cys Cys Ser Gln Trp Gly Trp Cys Gly Ser Thr Asp Glu Tyr
                         Internal
                              40
Cys Ser Pro Asp His Asn Cys Gln Ser Asn Cys Lys Asp
                       C-terminal
```

FIG.1A

| PCR Primer | Primer Sequence | Complexity of the Primer |
|---|---|---|
| N-terminal: | 5' AAGCTTGARCARTGYGGNMGNCARGC 3' | 512 |
| Internal: | 5' CCRCACCANCCCCAYTG 3' | 16 |
| C-terminal: | 5' GGATCCCARTTNSWYTGRCARTTRTG 3' | 512 |

FIG.1B

```
1    GGAAGAGTT  ATG AAT ATA TTT ATA GTT GTT TTA TTA TGT TTA ACA GGT
                Met Asn Ile Phe Ile Val Val Leu Leu Cys Leu Thr Gly
                    -15                 -10                      -5

49   GTT GCA ATT GCT GAG CAA TGT GGT CGG CAA GCA GGT GGC AAG CTC TGC
     Val Ala Ile Ala Glu Gln Cys Gly Arg Gln Ala Gly Gly Lys Leu Cys
                 1               5                       10

97   CCC AAT AAC CTA TGT TGT AGC CAG TGG GGG TGG TGT GGC TCC ACT GAT
     Pro Asn Asn Leu Cys Cys Ser Gln Trp Gly Trp Cys Gly Ser Thr Asp
             15                  20                  25

145  GAA TAT TGT TCA CCT GAT CAT AAC TGC CAA AGC AAT TGC AAA GAC AGC
     Glu Tyr Cys Ser Pro Asp His Asn Cys Gln Ser Asn Cys Lys Asp Ser
         30                  35                  40

193  GGC GAA GGT GTT GGT GGT GGA AGT GCT TCC AAC GTT CTT GCG ACG TAC
     Gly Glu Gly Val Gly Gly Gly Ser Ala Ser Asn Val Leu Ala Thr Tyr
     45                  50                  55                   60

241  CAT TTG TAT AAT TCA CAG GAT CAT GGA TGG GAC TTG AAT GCC GCA AGT
     His Leu Tyr Asn Ser Gln Asp His Gly Trp Asp Leu Asn Ala Ala Ser
                     65                  70                  75

289  GCA TAT TGC TCT ACA TGG GAT GCT AAC AAG CCA TAT TCA TGG CGG AGC
     Ala Tyr Cys Ser Thr Trp Asp Ala Asn Lys Pro Tyr Ser Trp Arg Ser
                 80                  85                  90

337  AAG TAT GGC TGG ACT GCA TTC TGC GGT CCC GTC GGA GCA CAC GGC CAA
     Lys Tyr Gly Trp Thr Ala Phe Cys Gly Pro Val Gly Ala His Gly Gln
                 95                  100                 105

385  TCC TCC TGT GGA AAG TGC TTG AGT GTG ACA AAT ACA GGG ACT GGA GCT
     Ser Ser Cys Gly Lys Cys Leu Ser Val Thr Asn Thr Gly Thr Gly Ala
             110                 115                 120

433  AAA ACG ACA GTG AGG ATT GTG GAT CAG TGT AGT AAT GGA GGA CTA GAT
     Lys Thr Thr Val Arg Ile Val Asp Gln Cys Ser Asn Gly Gly Leu Asp
                     130                 135                     140

481  TTG GAC GTG AAT GTT TTC CGT CAA CTG GAC ACA GAT GGG AAA GGA TAT
     Leu Asp Val Asn Val Phe Arg Gln Leu Asp Thr Asp Gly Lys Gly Tyr
                     145                 150                 155

529  GAA CGA GGT CAT ATT ACA GTG AAC TAC CAA TTT GTT GAT TGT GGA GAT
     Glu Arg Gly His Ile Thr Val Asn Tyr Gln Phe Val Asp Cys Gly Asp
                 160                 165                 170

577  TCC TTC AAT CCT CTA TTC TCC GTT ATG AAA TCA TCA GTA ATT AAT TAA
     Ser Phe Asn Pro Leu Phe Ser Val Met Lys Ser Ser Val Ile Asn  *
             175                 180                 185
```

FIG.2A

| | | | | |
|---|---|---|---|---|
| 625 | TAACATTGGA | TTGGATGTAT | GTTTAAGTCC | AATCGTAGTA | ACTAAGCTTC |
| 675 | TCAAGCAATA | AGCAACAACA | AGGCCAATTA | ATACTTCGTT | GGCCACTATA |
| 725 | AGAACTTGTG | AAATGTTATG | AGTTGTTGAA | AGAGTTTGTT | GTTGGAAATA |
| 775 | ATGGCATTTG | AGCCAGCTCT | GTAAGGTATT | GGTGAAGATT | ATTGGGAAGA |
| 825 | TCGGCTATCT | CTTTAGTGAG | ATATCCATTG | GTTTTCCCTT | CCTCCTTCCT |
| 875 | AAGTTGGGTG | TATTTGAGTT | ACGATTGTGT | GTATTTGAGT | TACGATTGTG |
| 925 | AGTTCAAGGT | TGAGTGGCTT | GTTATGAGTG | AAAAAAATAT | TTAATGTTTA |
| 975 | TATTTTTTTT | TTATATAATA | AAAGTTTTGT | TTGCAAAAAA | AAAA |

```
HEV1  M*NI****FIVVL*LC**LTGVAIAEQCGRQAGGKLCPNNLCCSQWGWCGSTDEYCSPDHNCQSNCKDSG
              ::            --  --   ---------:::------ ----  --:::---------- --
WIN2  MVKLSCGPILLALVLCISLTSVANAQQCGRQRGGALSGNNLCCSQFGWCGSTPEYCSPSQGCQSQCTGSG

HEV1  EGVG*GGSASNVLATYHLYNSQDHGWDLNAASAYCSTWDANKPYSWRSKYGWTAFCGPVGAHGQSSCGKC
           ---------:::   --   ---------------:::------------    --
WIN2  PDPGQGGSAQNVRATYHIYNPQNVGWDLNAVSAYCSTWDANKPYAWRSKYGWTAFCGPVGPRGRDSCGKC

HEV2  LSVTNTGTGAKTTVRIVDQCSNGGLDLDVNVFRQLDTDGKGYERGHITVNYQFVDCGDSFN*PLFSVMKSSVIN
      :::::::::::  :::::::::::::::::: :::::::  ::  ::::::::  --- ---   --
WIN2  LRVTNTRTGAQTTVRIVDQCSNGGLDLDINVFQQIDTDGVGNQQGHLIVNYQFVNCGDNVNVPLLSVV*DK***E
```

Wounding

FIG.5B

Ethephon

FIG.5C

ABA

FIG.5D

ABA

CDNA ENCODING A POLYPEPTIDE INCLUDING A HEVEIN SEQUENCE

GOVERNMENT RIGHTS

This application was funded under Department of Energy Contract DE-AC02-76ER01338. The U.S. Government has certain rights under this application and any patent issuing thereon.

BACKGROUND OF THE INVENTION

(1) Field of the Invention

The present invention relates to a novel cDNA encoding a novel polypeptide including a hevein sequence of 43 amino acids. In particular the present invention relates to a novel cDNA encoding a polypeptide of 204 amino acids.

(2) Prior Art

Latex of the rubber tree (Hevea brasiliensis) is produced by highly specialized cells known as laticifers (de Fay, E., et al., in Physiology of Rubber Tree Latex, eds. d'Auzac, J., Jacob, J. L., and Chrestin, H. (CRC, Boca Raton, Fla.), pp. 3-14 (1989)). The contiguous end walls of adjacent laticifer cells are perforated, thus forming an anastomosing system. Upon wounding, the common cytoplasmic content of these cells is expelled in the form of latex. Sealing of wound sites occurs by coagulation of the outflowing latex. This process involves bursting of the lutoid bodies (organelles of vacuolar origin) and subsequent interaction of the released cationic proteins with the negatively charged rubber particles (d'Auzac, J, et al., in Physiology of Rubber Tree Latex, eds. d'Auzac, J., et al., (CRC, Boca Raton, Fla.), pp. 59-88 (1989)). Wound plugging may be important in preventing entry of pathogens in the phloem.

One of the major proteins in the lutoid bodies of rubber tree latex is hevein (Archer, B. L., et al., J. Rubber Res. Inst. Malaya 21, 560-569 (1969)). Hevein is a small, single chain protein of 43 amino acids unusually rich in cysteine and glycine (Walujono, K., et al., in Proc. Internat. Rubber Conf. 518-531 (1975)). Recently, hevein has been shown to bind chitin and to inhibit the growth of several chitin-containing fungi (Van Parijs, J., et al., Planta 183:258-264(1991). It has therefore been suggested that hevein plays a role in the protection of wound sites from fungal attack (Van Parijs, J., et al., Planta 183:258-264(1991).

Various classes of chitin-binding proteins have been reported to contain polypeptide domains homologous to the hevein sequence. The lectins from the monocotyledonous species wheat, barley and rice are composed of four repetitive hevein-like domains (Wright, C. S., et al. Biochemistry 23, 280-287 (1984); Raikhel & Wilkins, Proc. Natl. Acad. Sci. USA 84, 6745-6749 (1988); Lerner, D. R., et al., Plant Physiol. 91, 124-129 (1989); and Wilkins, T. A., et al., Plant Cell 1, 541-549 (1989)), whereas a related lectin from the dicotyledonous Urtica dioica is thought to be composed of two such domains arranged in tandem (Chapot, M. P., et al., FEBS Lett. 195, 231-234 (1986)). Basic chitinases from bean (Broglie, K. E., et al., Proc. Natl. Acad. Sci. USA 83, 6820-6824 (1986)), tobacco (Shinshi, H., et al., Proc. Natl. Acad. Sci. USA 84, 89-93 (1987)) and poplar (Parsons, T. J., et al. Proc. Natl. Acad. Sci. USA 86, 7895-7899 (1989)) have a single hevein-like domain located at the amino-terminus which is fused to an unrelated carboxyl portion. Likewise, two wound-induced genes from potato encode proteins with a hevein-like domain located at the amino-terminus and a carboxyl-terminal extension that differs from the chitinase carboxyl-terminus (Stanford, A., et al., Mol. Gen. Genet. 215, 200-208 (1989)).

Hevein was first isolated from the latex of the rubber tree (Hevea brasiliensis) (Archer, B. L., et al, J. Rubber Res. Inst. Malaya 21, 560-569 (1969)). In the latex, hevein is present in lutoid bodies, which are small, vacuole-derived organelles. Hevein is a major protein in these particles representing up to 70% of the total protein content (Archer et al., previously cited). It is not known at present whether hevein occurs in other parts of the plant. Hevein is a monomer and has an apparent molecular weight of 9.5 kDa as determined by gel filtration and SDS-PAGE (Van Parijs, J., et al., Planta 183:258-264(1991). The amino acid sequence of hevein has a high degree of homology to WGA (Wright, C. S., et al., Biochemistry 23, 280-287 (1984)). The antifungal effects of hevein was examined on three different test organisms (Trichoderma hamatum, Phycomyces blakesleeanus, and Botrytis cinerea) by the hyphal growth inhibition assay. Dose-response experiments were carried out for each combination of hevein and fungus to determine the hevein concentration required for 50% inhibition of hyphal extension. Hevein caused 50% growth inhibition of T. hamatum, P. blakesleeanus, and B. cinerea at concentrations as low as 90, 300, and 250 µg/ml, respectively. Compared to tobacco chitinase (NTC), hevein is about one order of magnitude less active with T. hamatum and P. blakesleeanus, but more potent for inhibition of B. cinerea. Other fungi used in antifungal assays are Septoria nodorum, Pyricularia oryzae, Fusarium culmorum and Fusarium oxysporum which show a similar inhibition of hyphal growth as is shown for B. cinerea. Other chitin-binding lectins, WGA, Chelidonium majus agglutinin (CMA), Datura stramonium agglutinin (DSA) and Solanum tuberosum agglutinin (STA), did not affect fungal growth at concentrations below 2 mg/ml. To provide that the growth inhibiting effect of hevein was not due to contamination by chitinases or other compounds, this protein was subjected to several inhibitory treatments. The antifungal activity of hevein, and tobacco chitinase were reversed by addition of the specific ligand chitotriose (2 mM). However, hevein retained its antifungal properties when heated for 10 minutes at 90° C., whereas chitinase activity was completely destroyed by the same treatment. Therefore, this small-sized chitin-binding protein, hevein has antifungal properties and represents a promising target gene for possible applications in genetic engineering experiments.

The hevein protein represents a promising target gene for genetic engineering experiments. First, this protein has been shown to be a potent inhibitor of fungal growth, and may thus contribute to the plant's own resistance to fungal infection. On a per gram basis, its antifungal potency is comparable to that of phytoalexins, which inhibit fungal growth in the concentration range of 50 to 100 µg/ml (Weinstein, L. I., et al., Plant Physiol., 68, 358-363 (1981)).

OBJECTS

It is therefore an object of the present invention to provide a novel cDNA clone which encodes a novel peptide including a hevein peptide sequence and having an extensive carboxyl-terminal portion not present in mature hevein isolated from the rubber plant. Further, the present invention relates to novel fusion proteins that bind to chitin using the novel peptide as part of the fusion protein. Further, it is an object of the present invention to provide a novel method for binding chitin using the novel peptide. These and other objects will become increasingly apparent from the following description and the drawings.

IN THE DRAWINGS

FIGS. 2A and B show a nucleotide and deduced amino acid sequence of the hevein cDNA clone (HEV1). The deduced amino acid sequence is numbered under each line. Numbers on the left refer to the nucleotide sequence. Numbers 1 to 43 indicate the mature hevein domain. The two stop codons at the end of the coding region are marked with an asterisk. The potential polyadenylation signal is underlined.

FIGS. 5A, B, C and D show the effect of stress treatments on the accumulation of hevein transcripts. Total RNA (15 μg per lane) was isolated from leaves (LF), stems (ST) and latex (LT) of either untreated (−) or treated (+) rubber tree plants. (A) Treatment: wounding. Probe: coding region of HEV1. (B) Treatment: ethephon (0.1%). Probe: coding region of HEV1. (C) Treatment: 50 μM ABA. Probe: coding region of HEV1. (D) Treatment: 50 μM ABA. Probe: beta-ATPase cDNA.

FIG. 6 shows a SDS-PAGE analysis of amylose chromatography purified fusion proteins. Lane 1: MBP; Lane 2: N-terminal HEV1-MBP; Lane 3: C-terminal HEV1-MBP; Lane 4: full length HEV1-MBP; Lanes S: molecular weight markers (rabbit phosphorylase B, 97.4 kDa; bovine serum albumin, 66 kDa; egg albumin, 45 kDa; bovine carbonic anhydrase, 29 kDa; soybean trypsin inhibitor, 21 kDa; lysozyme, 14 kDa). Samples were run on precast Phastgel 10-15 (Pharmacia, Piscataway, N.J.) and developed by Coomassie Blue R350 staining.

GENERAL DESCRIPTION

The present invention relates to a cDNA clone, referred to as HEV1, as carried in E. coli ATCC 68363 which encodes a protein.

Figure 2B:
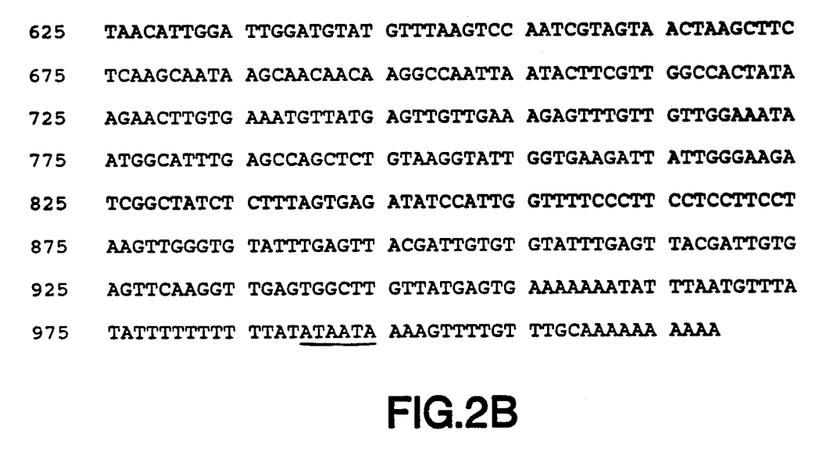

Further, the present invention relates to a method for the binding to chitin of an amount of a compound selected from the group consisting of a peptide having a sequence of 204 amino acids as shown in FIG. 2 and subfragments of the peptide which binds the chitin.

Further, the present invention relates to a method for the reversible binding on chitin of fusion proteins containing the 43 amino acids of the hevein peptide. The method is demonstrated using an N-terminal HEV1-MBP fusion protein and can be used for fusion protein purification purposes.

Also the present invention relates to a method for detecting the presence of hevein peptide sequence in plant material, which comprises: providing a selected part of the plant material for detection; isolating RNA from the plant material; and probing the RNA with a cDNA so that the RNA binds to the cDNA when there is homology, wherein the cDNA is derived from E. coli ATCC 68363, and has an open reading frame of 204 amino acids which detects the presence of hevein RNA.

Finally, the present invention relates to a method for detecting the presence of hevein peptide sequences in plant material, which comprises: providing a selected part of the plant material for detection; isolating RNA from the plant material; and probing the RNA with a cDNA so that the RNA binds to the cDNA where there is homology, wherein the cDNA is derived from the cDNA shown in FIG. 2 which detects the presence of hevein peptide sequences.

The cDNA is deposited as a plasmid in E. coli ATCC 68363. The deposit is under the Budapest Treaty and is available upon request by accession number and genus and species name.

The protein of the present invention can be used in an amount between about 90 μg/ml and 500 μg/ml to inhibit growth of fungi. The chitin can be in fungi. The amount of the protein of the present invention which is used is equivalent to the amount of hevein which would be used to inhibit fungi.

The following is a discussion of the isolation of the cDNA clone and its use.

SPECIFIC DESCRIPTION

The following description shows the preparation of the double stranded cDNA from RNA, the insertion of the cDNA into E. coli and then the isolation of a single clone encoding the novel polypeptide. The regulation of hevein expression in the plant is also described using the cDNA as a probe. Finally, a description is given of the production of fusion proteins between a bacterial maltose binding protein and the protein (or subfragments) encoded by the cDNA, and the affinity of one of the fusion proteins for chitin.

Materials and Methods

Plant Material. Latex for construction of the cDNA library was obtained from rubber trees twenty years of age (*Hevea brasiliensis* RRIM600). These trees were regularly tapped and were treated with 0.1% "ETHEPHON" (2-chloroethylphosphonic acid) two weeks prior to tapping, which has been shown to enhance latex production (Coupe, M., et al., in Physiology of Rubber Tree Latex, eds. d'Auzac, J., et al., (CRC Press, Inc., Florida) pp. 295-319 (1989)). For Northern blot analysis to study the regulation of hevein expression, seedlings four months of age of *Hevea brasiliensis* RRIM600, grown in a growth chamber were used.

RNA Isolation and Construction of Latex-specific cDNA Library. Total RNA from the latex was extracted as described by Kush, A., et al., Proc. Natl. Acad. Sci. USA 87, 1787-1790 (1990) and poly (A)+ RNA was purified by oligo-dT cellulose affinity chromatography using the method of Siflow, C. D., et al., Biochem. 18, 2725-2731 (1979). Double-stranded cDNAs were prepared from 10 μg of poly(A)+ RNA according to Gubler and Hoffman (Gubler, U., et al., Gene 25, 263-269 (1983)) with the cDNA "SYNTHESIS SYSTEM" (Amersham, Arlington Heights, Ill.). The cDNA was ligated into lambda gt10 (Stratagene, San Diego, Calif.) with EcoRI linkers (New England Biolabs, Beverly, Mass.) and packaged in vitro using "GIGAPACK GOLD" (Stratagene). The host strain used for screening plaques was *E. coli* C600hfl (Stratagene, San Diego, Calif.).

Polymerase Chain Reaction (PCR). The oligonucleotide mixtures were synthesized by the Macromolecular Structure, Sequencing and Synthesis Facility at Michigan State University. DNA amplification was carried out on a Perkin-Elmer thermal cycler, in a 100-μl vol containing 50 mM KCl, 10 mM Tris-HCl (pH 8.3), 1.5 mM $MgCl_2$, 0.01% gelatin, 1 μM of each primer, 200 μM each dNTP, 2.5 units of *Thermus aquaticus* polymerase (Cetus, San Francisco, Calif.), and 1 μg of lambda gt10 cDNA library. Twenty-five cycles of amplification were performed (96° C. for 1 min, 47° C. for 2 min, 72° C. for 3 min with a final polymerase extension step at 72° C. for 7 min) and 10% of the product was analyzed on a 1% agarose (SeaKem; FMC) gel. The product was excised from the gel and reamplified. The reamplified band was isolated as above, digested with EcoRI and BamHI, and ligated into pUC119 (Viera, J., et al., Methods Enzymol. 153, 3-11 (1987)).

Isolation of the HEV1 Clone and DNA Sequencing. The amplified PCR fragment was labeled with [$^{32}$P]dATP by the random primer technique (Feinberg, A. P., et al., Anal. Biochem. 137, 266-267 (1985)). Approximately 200,000 plaque forming units of the lambda gt10 cDNA library were screened with the [$^{32}$P]-labeled PCR product as the probe by in situ plaque hybridization at high stringency conditions (Raikhel, N. V., et al., Planta 176, 406-414 (1988)). Plaques producing positive signals were selected and rescreened using the same probes under the same conditions. Inserts from purified plaques were subcloned into the EcoRI site of pUC119 and sequenced by the dideoxynucleotide chain termination method (Sanger, F., et al., Proc. Natl. Acad. Sci. USA 74, 5463-5467 (1977)) using [alpha-$^{35}$S]-dATP and 7-deaza-dGTP in place of dGTP (Mizusawa, S., et al., Nucl. Acids Res. 14, 1319-1324 (1986)). The complete sequence of the clones was obtained by sequencing overlapping deletions generated by T4 DNA polymerase (Dale, R. M. K., et al., Methods Enzymol. 155, 204-214 (1987)). Sequence analysis was performed by "EDITBASE" software (courtesy of N. Nielsen, Purdue University, West Lafayette, Ind.).

Northern blot analysis. Total RNA from the various parts of four-month old seedlings was prepared by the method of Kirk and Kirk (Kirk, M. M.,et al., Cell, 41, 419-428 (1985)) using aurincarboxylic acid. Microtapping was done to collect the latex, by making incision on the stem and collecting the drops of exuded latex. Total RNA was separated in 2% agarose gels containing 6% formaldehyde and blotted onto "HYBOND-N-MEMBRANE" (Amersham, Arlington Heights, Ill.). The conditions of blotting, prehybridization and hybridization were as recomnended by the manufacturer. Blots were hybridized with hevein insert labeled by the random primer method of Feinberg (Feinberg, A. P., et al., Analy Biochem. 137, 266-267 (1985)).

Wounding of Hevea Stems, Ethephon and ABA applications. For wounding, a spiral cut about 0.5 cm deep was made on the stem of seedlings and RNA was extracted from stem, leaf and latex 24 hours later. "ETHEPHON" (0.1%) was sprayed on young seedlings and RNA was isolated from stem, leaf and latex after 24 hours. 50 μM abscisic acid (ABA), dissolved in sterile water/0.01% ethanol was sprayed on the plant and RNA was extracted from stems, leaf and latex after 24 hours as described above. Control plants were sprayed with water/ethanol solution alone.

Overexpression of amino-, carboxyl-terminal and full length HEV1 cDNA clone in *E. coli*

Figure 6:
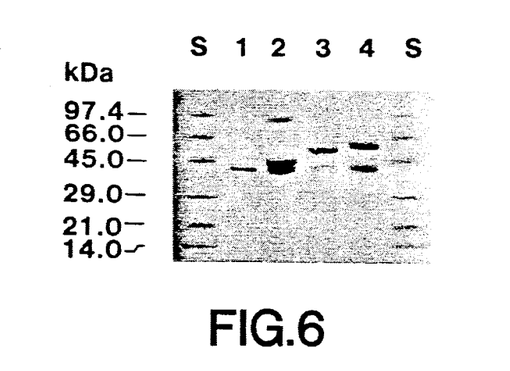

The amino-, carboxyl-terminal and the full length HEV1 cDNA clone were subcloned in the plasmid pIH821 (New England Biolabs, Beverly, Mass.) coding for a maltose-binding fusion protein (MBP). The MBP vectors were grown at 37° C. in a 1 liter culture of rich broth to a cell density of $4 \times 10^8$ cells/ml. IPTG (isopropyl-beta-D-galactoside) was added to a final concentration of 0.3 mM and the culture was grown for an additional 4 hours at 37° C. The cells were harvested by centrifugation ($4000 \times g$, 10 min) and resuspended in 50 ml of phosphate buffered saline (pH 7.0) containing 0.2% Tween-20, 5 mM DTT, 10 mM EDTA, 10 mM EGTA and 1 mM PMSF. After a freeze-thaw cycle the cells were sonicated at 75 W for 2 min. After removal of cellular debris by centrifugation ($9000 \times g$, 30 min) the crude extract was diluted 5-fold in 10 mM sodium phosphate (pH 7.0), 0.5M NaCl, 0.25% Tween-20. The extract was subjected to affinity chromatography on a column (2.6 cm $\times$ 4 cm) of cross-linked amylose (New England Biolabs, Beverly, Mass.) according to the manufacturer's instructions. The results are shown in FIG. 6.

Affinity chromatography on chitin

Figure 7:
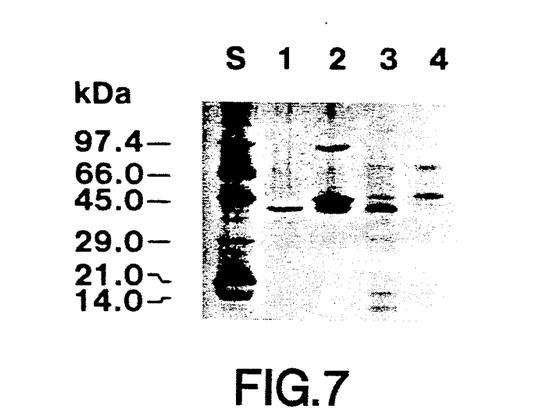
FIG. 7 shows SDS-PAGE analysis of affinity chromatography on chitin of purified N-terminal HEV1-MBP fusion protein. Lane 1: MBP; Lane 2: N-terminal HEV1-MBP preparation prior to affinity purification on chitin column; Lane 3: unbound fraction; Lane 4: bound fraction desorbed by 50 mM 1,3 diaminopropane; Lane M: molecular weight markers (see FIG. 6). Samples were run on precast Phastgel 10-15 (Pharmacia, Piscataway, N.J.) and developed by silver staining.

Chitin was prepared by reacetylation of chitosan (Sigma, St. Louis, Mo.) as described by Molano et al (Molano et al, Anal. Biochem, 83, 648-656 (1977)) and washed thoroughly with 500 mM acetic acid, 0.1M HCl, 0.1M NaOH; 8M urea/0.1M NaOH, and 50 mM 1,3-diaminopropane. 50 μg of N-terminal HEV1-MBP fusion protein, affinity purified on an amylose column, was loaded on a minicolumn (0.25 ml volume) of chitin, and recycled over the column 5 times. The column was washed with 5 ml of sodium acetate buffer containing 0.5M NaCl and 5 ml of phosphate buffed saline. The bound fraction was desorbed with 50 mM 1,3-diaminopropane. The unbound and desorbed fractions were dialyzed extensively against distilled water, lyophilized and analyzed by SDS-PAGE. The results are shown in FIG. 7.

RESULTS

Figure 1A:
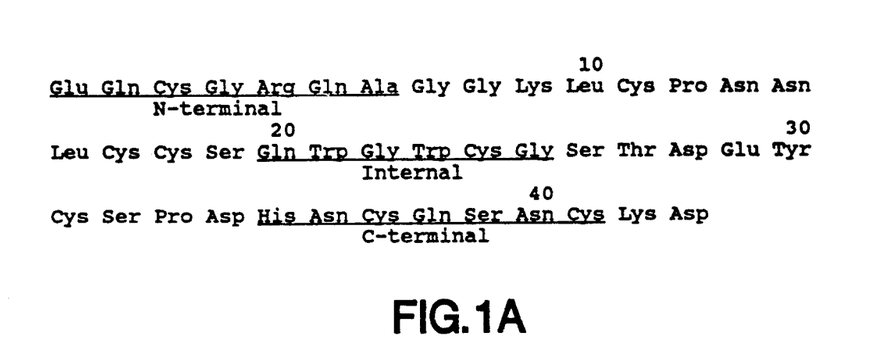
FIGS. 1A and B show a complete amino acid sequence of mature hevein and nucleotide sequences of the primers used in polymerase chain reaction (PCR). A) Amino acids of hevein are depicted as three letter codes. Peptide sequences corresponding to the PCR primers are indicated by underlining. B) The nucleotide sequences of the PCR primers are represented by the following codes: M, either A or C; N, either A, G, C, or T; R, either A or G; S, either C or G; W, either A or T; Y, either T or C. The orientation relative to hevein mRNA is sense for the amino-terminal primer, and antisense for the internal and carboxyl-terminal primers. Restriction enzyme sites are underlined (HindIII) or, double underlined (BamHI).
Figure 1B:
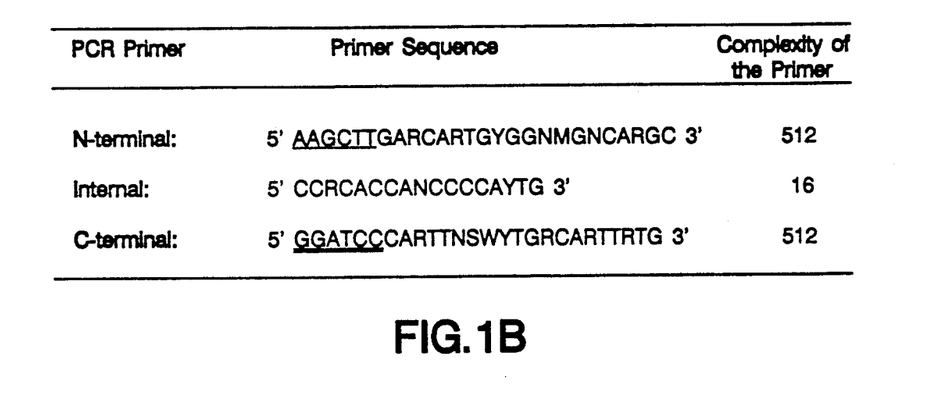

Isolation and Sequence of a Full-Length cDNA Clone. The primary structure of the hevein protein has been previously reported (FIG. 1, A, Walujono, K., et al., in Proc. Internat. Rubber Conf. 518-531 (1975)). Three sets of oligonucleotide primers corresponding to the amino-terminal, carboxyl-terminal and internal regions of the hevein protein (FIG. 1, A) were synthesized. Each primer was a degenerate mixture of oligonucleotides encoding the underlined amino acids (FIG. 1, A, B). The amino-terminal and carboxyl-terminal primers were used in the PCR. The template for the PCR was phage DNA prepared from a *Hevea brasiliensis* latex cDNA library in lambda gt10. The amplified DNA fragment was identified by agarose gel electrophoresis as a band of the expected size of 140 base pairs. To confirm that the amplified DNA was derived from a portion of the hevein cDNA, the 140 base pair fragment was gel-purified and reamplified with the amino-terminal and internal primers. The predicted size of the reamplified PCR product was 80 base pairs. To rescue the 140 base pair fragment the entire PCR reaction was digested with appropriate restriction enzymes (recognition sites for HindIII and BamHI were included at the 5' end of the amino-terminal and carboxyl-terminal primers, respectively, FIG. 1, B) and cloned into the plasmid pUC119 between the BamHI and HindIII sites. Recombinant clones were propagated in *E. coli* and several isolates containing inserts of the appropriate molecular size were chosen. Sequencing of the inserts revealed that each contained an open reading frame corresponding to the hevein sequence.

For isolating the full-length hevein cDNA clone, a lambda gt10 cDNA library was synthesized from poly-(A)+RNA isolated from the latex of *Hevea brasiliensis*. Approximately 200,000 primary recombinant phages were screened with the 140-base pair PCR product. Eight positive clones were identified that contained inserts ranging from 1 to 1.2 kb. Dideoxy sequencing of the longest cDNA (HEV1) showed that this clone was 1018 nucleotides long and contained an open reading frame of 204 amino acids including 17 amino acids at the amino terminus that are not present in the mature protein (FIG. 2, Walujono, K., et al., in Proc. Internat. Rubber Conf. 518-531 (1975)). These residues comprised a predicted signal sequence structure (von Heijne, G., Mol. Biol. 184, 99-105 (1985) cleavage site between the −1 and +1 amino acid matches the amino terminus found by protein sequence analysis (Walujono, K., et al., in Proc. Internat. Rubber Conf. 518-531 (1975)). The deduced amino acid sequence of the region following the putative signal peptide (FIG. 2) is identical to the known 43 amino acid sequence of hevein (open box in FIG. 2, Walujuno, K., et al., in Proc. Internat. Rubber Conf. 518-531 (1975)). In addition to the putative signal sequence and the known hevein protein, the cDNA clone encoded a protein with an additional 144 amino acids (FIG. 2) extending beyond the hevein sequence. The sequence is deposited in Gene Bank database (Gene Bank Submissions, Mail Stop K710, Los Alamos National Laboratory, Los Alamos, N.M. 87545) Accession No. M36986.

The 3'-untranslated region contained two consecutive in-frame termination codons (TAA, TAA, FIG. 2, stars) and a 316 nucleotide untranslated region. A potential polyadenylation signal (AATAAA, underlined in FIG. 2) began at position 991 and was followed 11 nucleotides downstream by a short poly(A) tail.

Figure 3:
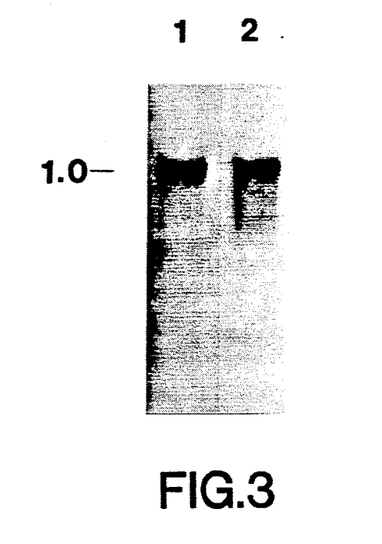
FIG. 3 shows a Northern blot analysis of total RNA from rubber tree latex. lane 1: the blot was probed with a $^{32}$P-labelled DNA fragment corresponding to the amino-terminal region of HEV1 (nucleotides 61-182, see FIG. 2). Lane 2: the same blot was stripped and reprobed with a $^{32}$P-labelled DNA including the carboxyl-terminal portion of HEV1 (nucleotides 239-610, see FIG. 2).

Northern blot analysis. To confirm the identity of the HEV1 cDNA clone, total RNA extracted from *Hevea brasiliensis* latex was fractionated by agarose-formaldehyde gel electrophoresis and transferred to a nitrocellulose filter. A 1.0-kb mRNA was detected (FIG. 3, lane 1) by hybridization with the nucleotide fragment that was specific for the amino-terminus sequence of hevein. The same blot was reprobed with the C-terminal region of the HEV1 cDNA clone which hybridized to the same 1.0-kb mRNA species (FIG. 3, lane 2).

Figure 4:
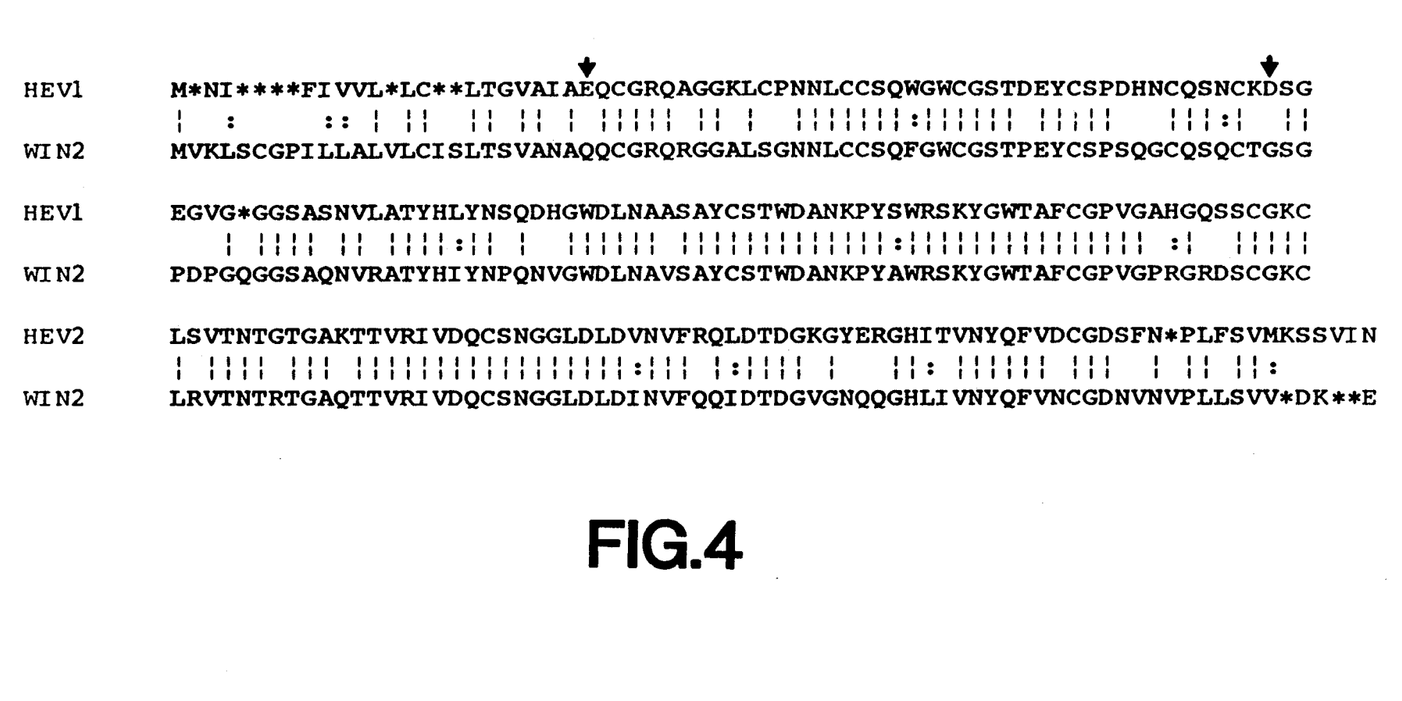
FIG. 4 shows a comparison of the amino acid sequences deduced from the cDNAs of HEV1 and WIN2. Identical amino acids are marked by vertical lines and conservative substitutions by two dots. Gaps introduced for alignment of homologous domains are indicated by asterisks. The first and the last amino acids of the amino-terminal domain (mature hevein) are designated with the arrows.

HEV1 is Similar to Wound-Inducible Genes in Potato. A comparison of the primary structure of the HEV1 encoded protein with the wound-induced genes WIN1 and WIN2 of potato (Stanford, A., et al., Mol. Gen. Genet. 215, 200-208 (1989)) revealed a high degree of homology in both the amino-terminal and carboxyl-terminal portions (FIG. 4). The overall sequence identity between the HEV1 and the WIN deduced amino acid sequences was as high as 65% (HEV1-/WIN1) and 68% (HEV1/WIN2). No sequence conversation could be observed in the putative signal-peptide region.

Figure 5A:
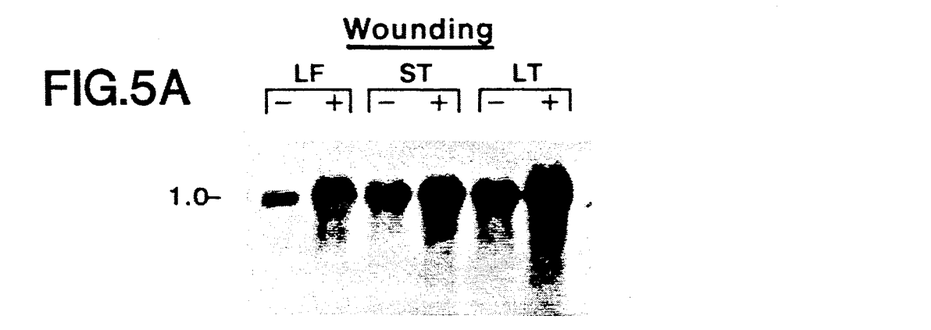
Figure 5B:
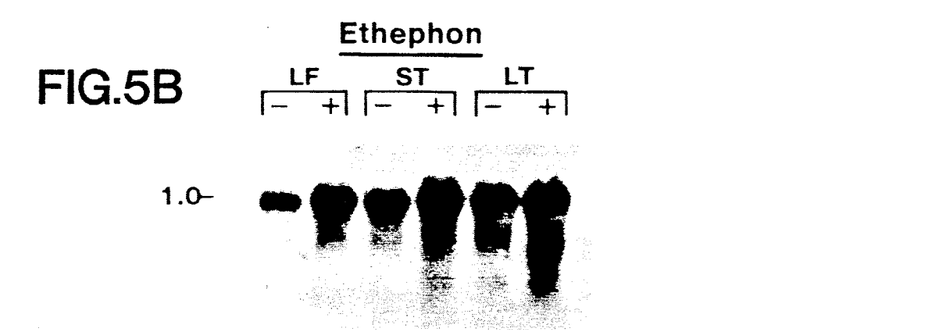
Figure 5C:
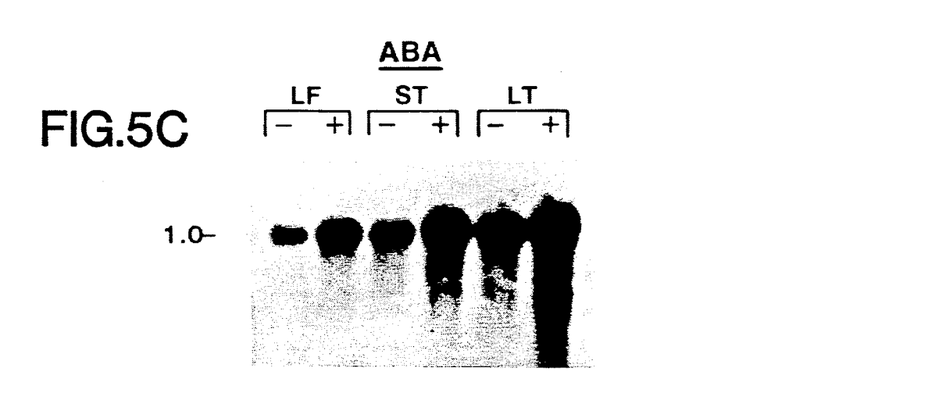
Figure 5D:
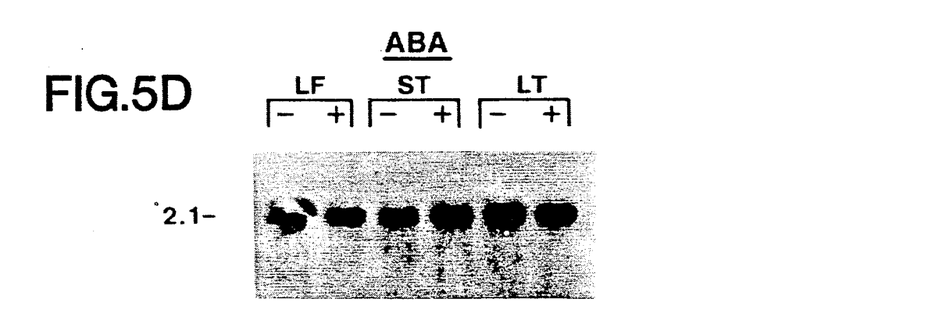

Organ-specific Expression of Hevein mRNA. The expression of hevein mRNA was examined by Northern blot analysis. RNA was isolated from intact leaves, stems, roots and latex from young seedlings of *Hevea brasiliensis*. Hevein mRNA accumulates in leaves, stems and latex (FIG. 5, A, B, C). However, no hevein mRNA was detected in roots.

Accumulation of Hevein mRNA upon Wounding, ABA and Ethylene Treatments. To investigate the extent that hevein mRNA is induced by wounding and hormone treatment, young rubber tree seedlings were locally wounded by applying a spiral cut along their stem. After 24 hours the RNA was extracted from leaves, stems and latex of both intact and wounded plants. Northern blot analysis (FIG. 5, A) showed that in intact plants, hevein was expressed in all three tissues, reaching the highest expression levels in the latex. However, in leaves, stems and latex of wounded plants the steady-state amounts of hevein mRNA transcripts increased 5 to 10-fold relative to the levels in tissues isolated from control plants (FIG. 5, A). A similar increase in hevein mRNA in leaves, stem and latex was observed 24 hours after spraying rubber tree seedlings with either 0.1% ethephon (FIG. 5, B) to produce ethylene, or 50 μM ABA (FIG. 5, C). As a control for the specificity of the observed responses, each blot was reprobed with a probe for beta ATPase (Boutry, M., et al., EMBO Journal 4, 2159-2165 (1985)) which is known to be constitutively expressed in plants (Kush, A., et al., Proc. Natl. Acad. Sci. USA 87, 1787-1790 (1990)). None of the treatments affected the level of beta ATPase massage in any tissue (FIG. 5, D). No hevein mRNA could be detected in roots from intact, wounded or hormone treated plants (results not shown).

Overexpression and affinity purification on chitin column.

The full length protein encoded by HEV1, (187 aa), its N-terminal portion (first 43 aa) and its C-terminal portion (last 144 aa) were produced as fusion proteins linked to a bacterial maltose binding protein ( . . . aa) by overexpression in *E. coli*. The Mr of the amylose-affinity purified fusion proteins was as predicted for the gene fusion sequences (45 kDa for N-terminal HEV1-MBP, FIG. 6, lane 2; 55 kDa for C-terminal HEV1-MBP, FIG. 6, lane 3; and 60 kDa for full length HEV1-MBP, FIG. 6, lane 6). All affinity purified preparations were contaminated by MBP (Guan et al, Gene, 67: 21-30 (1988)), migrating on the SDS-PAGE gel at about 40 kDa (FIG. 6, line 1).

The purified N-terminal HEV1-MBP preparation was subjected to chitin affinity chromatography. Relative to the N-terminal HEV1-MBP preparation prior to chitin affinity chromatography (FIG. 7, lane 2), the unbound fraction (FIG. 7, lane 3) is depleted in N-terminal-MBP and enriched in MBP. The desorbed fraction (FIG. 7, lane 4) is highly enriched in N-terminal HEV1-MBP.

The amino acid sequence of hevein was deduced from a cDNA clone designated HEV1. The first 43 deduced amino acids are identical to the known hevein sequence as determined by direct amino acid sequencing (Walujono, K., et al., in Proc. Internat. Rubber Conf. 518-531 (1975)). However, the protein deduced from the HEV1 cDNA clone has a striking feature. The DNA sequence of HEV1 encodes a protein that extends 144 amino acids beyond the carboxyl terminus of the hevein protein. Northern blot analysis using the amino-terminal and carboxyl-terminal portions of the HEV1 cDNA clone as probes indicated that they hybridize to the same mRNA species. The results of the Northern analysis and the fact that amino acids deduced from the amino-terminal portion of HEV1 cDNA clone are identical to the known hevein sequence strongly suggest that the HEV1 cDNA clone encodes the hevein protein. The difference in polypeptide length between purified hevein and the hevein deduced from the cDNA clone may be the consequence of a post-translational modification. Thus, cleavage of the 187 amino acid pro-protein may lead to the formation of a mature 43 amino acid hevein and a 144 amino acid carboxyl-terminal polypeptide. Alternatively, cleavage of the carboxyl-terminal portion may occur during the purification of hevein and the mature protein may actually correspond to the full coding region of the HEV1 clone.

Mature hevein is found in the lutoid bodies of laticifers of rubber trees, an organelle analogous to the vacuole (Archer, B. L., et al., J. Rubber Res. Inst. Malaya 21, 560-569 (1969)). As predicted for proteins destined for entry into the endomembrane system of the secretory pathway, the deduced amino acid sequence of the hevein cDNA clone contains a signal sequence which is cotranslationally cleaved. The predicted cleavage site between an alanine (A, −1) and a glutamic acid residue (E, +1), corresponds exactly to the amino terminus of the mature hevein. HEV1 contains two termination codons and a 3′-untranslated region. A potential polyadenylation signal represents a consensus motif AAUAAA followed by a short poly(A) tail.

The amino-terminus of the protein encoded by HEV1 cDNA shows extensive homology to the N-acetyl glucosamine-oligomer-specific lectins from wheat (Raikhel, N. V., et al., Proc. Natl. Acad. Sci. USA 84, 6745-6749 (1987)), barley (Lerner, D. R., et al., Plant Physiol. 91, 124-129 (1989)), rice (Wilkins, T. A., et al., Plant Cell, 1, 541-549 (1989)), and *Urtica dioica* (Chapot, M. P., et al., FEBS Lett., 195, 231-234 (1986)), to the amino-termini of basic chitinases (Broglie, K. E., et al., Proc. Natl. Acad. Sci. USA 83, 6820-6824 (1986); and Shinshi, H., et al., Proc. Natl. Acad. Sci. USA 84, 89-93 (1987)) and polypeptides encoded by wound-induced genes (WIN1 WIN2) of potato (Stanford, A., et al., Mol. Gen. Genet. 215, 200-208 (1989)). Except for the WIN1 and WIN2 polypeptides, all of these proteins have been shown to bind chitin, suggesting that the hevein-like 43 amino acid domain they share is responsible for their carbohydrate-binding properties. This assumption is supported by the observation that acidic chitinases from tobacco, which mainly differ from their basic isoforms by the absence of the amino-terminal hevein-like domain (Hooft van Huijsduijnen, R. A. M., et al., Plant Mol. Biol. 9, 411-420 (1987); and Shinshi, H., et al., Plant Mol. Biol. 14, 357-368 (1990)), do not bind to a chitin column (W. Broekaert, unpublished results), and by the fact that mature hevein itself binds to chitin Van Parijs, J., et al., Planta 183:258-264(1991). Moreover, we have now shown that the 43 amino-acid N-terminal domain of HEV1 is capable of containing chitin binding properties. The carboxyl-terminal portion of the HEV1 encoded protein shows homology to the carboxyl-termini of proteins deduced from WIN1 and WIN2 genes, but not to those of chitinases nor to chitin-binding lectins. The carboxyl-terminus of HEV1 shows 74% homology to the deduced amino acid sequences from the WIN1 gene and 79% to the WIN2 gene. The amino terminus (minus the putative signal sequence) has 72% and 74% homology to WIN1 and WIN2, respectively. These levels of homology suggest that the carboxyl-terminal portion of these proteins serves a function as important as that of the amino terminus. The study of the role of both HEV1 domains and the relevance of the presumed post-translational cleavage is in progress in transgenic tobacco and tomato plants.

Wheat germ agglutinin has been demonstrated to act as an anti-nutrient factor for insect larvae (Murdock, L. L., et al., Phytochemistry 29, 85-89 (1989)). In addition mature hevein Van Parijs, J., et al., Planta 183: 258-264(1991)) as well as the stinging nettle lectin (Broekaert, W. F., et al., Science 245, 1100-1102 (1989)) and chitinases (Schlumbaum, A., et al., Nature 324, 365-367 (1986); and Broekaert, W. F., et al. Physiol. Mol. Plant Pathol. 33, 319-331 (1988)) are known inhibitors of fungal growth in vitro. Hence, it appears that in a broad sense this class of related chitin-binding proteins may serve to protect plants from attack by a broad range of potential pathogens.

Wounding, or exogenous application of the stress-related hormones ABA or ethylene, leads to increased steady-state levels of hevein mRNA. This response was observed in leaves, stem and stem-tapped latex, but not in roots. It is not known at present whether the accumulation of hevein transcripts in leaves and stems is confined to the laticifers or whether other tissues are involved as well. The observed response may be systemic since transcripts accumulate in unwounded leaves upon wounding of the stems. Systemic responses to wounding have previously been reported for other genes such as those encoding proteinase inhibitors in tomato (Graham, J. S., et al., Planta 169, 399-405 (1986)) and potato (Pena-Cortes, H., et al., Proc. Natl. Acad. Sci. USA 86, 9851-9855 (1989)), and chitinase-related genes in poplar (Parsons, T. J., et al., Proc Natl. Acad. Sci. USA 86, 7895-7899 (1989)).

Wounding elicits a number of physiological changes which are accompanied by an enhanced rate in ethylene biosynthesis (Boller, T., et al., Nature 286, 259-260 (1980); Yang, S. F., et al. Annu. Rev. Plant Physiol. 35, 155-189 (1984)) and increases in several wound-induced mRNAs (Henstrand, J. M., et al, Plant Physiol. 91, 157-162 (1990)). Both wounding and exogenous application of ethylene have been shown to cause accumulation of mRNAs of defense-related proteins such as chitinases in beans (Broglie, K. E., et al., Proc. Natl. Acad. Sci. USA 83, 6820-6824 (1986); and Hedrick, S. A., et al., Plant Physiol. 86, 182-186 (1988)) and hydroxyproline-rich glycoproteins in carrots (Ecker, J. R., et al., Proc. Natl. Acad. Sci. USA 84, 5202-5206 (1987)). However, it is not known to what extent wound-induced ethylene activates gene expression. Experiments with inhibitors of ethylene synthesis indicate that wound-induced ethylene does not generally play a direct role in signal transduction in wounded tissues per se (Henstrand, J. J., et al., Plant Physiol. 91, 157-162 (1990), but may act in systemic activation of wound-inducible genes in undamaged tissues. Recently, ABA has been implicated in the wound-induced response of protease inhibitor II in potato and tomato (Pena-Cortes, H., et al., Proc. Natl. Acad. Sci. USA 86, 9851-9855 (1989)). Both ethylene and ABA can mimic the wound-induced accumulation of hevein steady-state mRNAs in different rubber tree tissues. These data support the hypothesis that several separate signal transduction pathways can lead to the activation of wound-induced and/or defense related genes in plants (Ecker, J. R., et al., Proc. Natl. Acad. Sci. USA 84, 5202-5206 (1987); and Henstrand, J. M., et al. Plant-Physiol. 91, 157-162 (1990)).

MBP vectors overexpressed cloned fusion proteins and they were affinity purified using an amylose resin.

The amino-terminal HEV1-MBP fusion protein was shown to exhibit chitin-binding activity, whereas MBP itself showed no affinity to chitin. This example demonstrates that fusion of the amino-terminal HEV1 to a polypeptide confers chitin-binding properties to the resulting fusion protein, which can hence be purified by chitin-affinity chromatography.

FIG. 1 shows cDNA sequences 1 to 1018. Sequences 1 to 204 expresses a polypeptide including hevein.

It is intended that the foregoing description be only illustrative of the present invention and that the present invention be limited only by the hereinafter appended claims.

We claim:

1. A protein free of other proteins naturally occurring with the protein, said protein selected from the group consisting of the sequence of 204 amino acids shown in FIG. 2 and subfragments of said sequence larger than the 43 amino acid hevein sequence which includes the hevein sequence and which binds chitin.

2. A method for inhibiting growth by binding chitin in a fungus which comprises exposing the chitin of the fungus to an amount of a protein free of other proteins naturally occurring with the protein, said protein selected from the group consisting of the sequence of 204 amino acids shown in FIG. 2 and subfragments of said sequence larger than the 43 amino acid hevein sequence which includes the hevein sequence, which protein binds the chitin and inhibits fungal growth.

* * * * *